United States Patent
Barley et al.

(10) Patent No.: US 9,681,923 B2
(45) Date of Patent: *Jun. 20, 2017

(54) MEDICAL ULTRASOUND DEVICE WITH FORCE DETECTION

(75) Inventors: Maya Ella Barley, Eindhoven (NL); Godefridus Antonius Harks, Eindhoven (NL); Szabolcs Deladi, Eindhoven (NL)

(73) Assignee: Koninklijke Philips N.V., Eindhoven (NL)

(*) Notice: Subject to any disclaimer, the term of this patent is extended or adjusted under 35 U.S.C. 154(b) by 0 days.

This patent is subject to a terminal disclaimer.

(21) Appl. No.: 13/393,244

(22) PCT Filed: Sep. 8, 2010

(86) PCT No.: PCT/IB2010/054048
§ 371 (c)(1),
(2), (4) Date: Feb. 29, 2012

(87) PCT Pub. No.: WO2011/033421
PCT Pub. Date: Mar. 24, 2011

(65) Prior Publication Data
US 2012/0165669 A1    Jun. 28, 2012

(30) Foreign Application Priority Data
Sep. 15, 2009  (EP) ................. 09170252 A

(51) Int. Cl.
*A61B 90/00* (2016.01)
*A61B 5/00* (2006.01)
(Continued)

(52) U.S. Cl.
CPC .......... *A61B 90/06* (2016.02); *A61B 5/6885* (2013.01); *A61B 8/12* (2013.01); *A61B 8/445* (2013.01);
(Continued)

(58) Field of Classification Search
USPC ................................. 600/437, 459
See application file for complete search history.

(56) References Cited

U.S. PATENT DOCUMENTS 7,578,789 B2    8/2009  Sandrin et al.
8,030,824 B2   10/2011  Knowles et al.
(Continued)

FOREIGN PATENT DOCUMENTS

CN      101283925 A    10/2008
EP         0329817       8/1992
(Continued)

OTHER PUBLICATIONS

Yokoyama, "Novel Contact Force Sensor Incorporated in Irrigated Radio frequency Ablation Catheter Lesion Size and Incidence of Steam Pop and Thrombus", Circ Arrhythmia Electrophysiol, (2008).
(Continued)

*Primary Examiner* — Rochelle Turchen

(57) ABSTRACT

A medical ultrasound device is disclosed. The device comprises an elongated body having a proximal end and a distal end region (1). One or more ultrasound transducers (4) for generating acoustic radiation are positioned in the distal end region, inside the elongated body. A transmission element (5) which is substantially transparent to acoustic radiation is positioned in the radiation path of the acoustic radiation, and a controller unit is operatively connected to the ultrasound transducer. The transmission element and the one or more ultrasound transducers are mounted so that an acoustic path length (8) between the transmission element (5) and the ultrasound transducer (4) varies with contact force (10) imposed to the distal end region. The controller unit detects the acoustic path length between the ultrasound transducer and the transmission element and determines the contact (Continued)

force from the detected acoustic path length. In an embodiment, the medical device is an ultrasound RF ablation catheter.

15 Claims, 5 Drawing Sheets

(51) Int. Cl.
　　*A61B 8/12* 　　　(2006.01)
　　*A61B 18/02* 　　(2006.01)
　　*A61B 18/12* 　　(2006.01)
　　*A61B 18/14* 　　(2006.01)
　　*A61B 17/00* 　　(2006.01)
　　*A61B 8/00* 　　　(2006.01)

(52) U.S. Cl.
　　CPC .......... *A61B 18/0206* (2013.01); *A61B 18/12* (2013.01); *A61B 18/1492* (2013.01); *A61B 2017/00106* (2013.01); *A61B 2090/065* (2016.02)

(56) References Cited

U.S. PATENT DOCUMENTS

| | | |
|---|---|---|
| 8,034,004 B2* | 10/2011 | Menne et al. .................. 601/4 |
| 8,876,699 B2 | 11/2014 | Sato et al. |
| 2003/0078498 A1* | 4/2003 | Lang et al. ................... 600/437 |
| 2004/0167499 A1 | 8/2004 | Grove et al. |
| 2008/0009750 A1 | 1/2008 | Aeby et al. |
| 2009/0149753 A1 | 6/2009 | Govari et al. |
| 2009/0177095 A1 | 7/2009 | Aeby et al. |
| 2009/0299180 A1 | 12/2009 | Lacoste |
| 2010/0168572 A1* | 7/2010 | Sliwa et al. ................. 600/439 |
| 2012/0165669 A1 | 6/2012 | Barley et al. |

FOREIGN PATENT DOCUMENTS

| | | |
|---|---|---|
| JP | 2009142653 A | 7/2009 |
| WO | 2008107842 | 9/2008 |

OTHER PUBLICATIONS

Okumura, "A systematical analysis of in vivo contact forces on virtual catheter tip/tissue surface contact during cardiac mapping and intervention", J Cardiovasc Electrophysiol, (2008).

* cited by examiner

MEDICAL ULTRASOUND DEVICE WITH FORCE DETECTION

FIELD OF THE INVENTION

The invention relates to a medical ultrasound device, such as a probe or catheter-based device. In particular the invention relates to such devices capable of detecting the contact force imposed to the distal end region of the device.

BACKGROUND OF THE INVENTION

Catheter-based surgery is advantageously used in various connections to treat body organs with minimal incision size and clearance of the organs. As an example, cardiac arrhythmias may be treated by various catheter-based ablation techniques to destroy arrhythmogenic parts of the cardiac tissue. Specifically, radio-frequency (RF) ablation, high intensity focused ultrasound (HIFU) or cryo-ablations of the tissue are commonly used.

In connection with the ablation process of cardiac tissue, it has recently been realized that the contact force between an ablation catheter's tip and the cardiac tissue is a highly important variable that must be controlled. It has been shown that the contact force is a determinant with respect to the lesion size, cf. "Novel Contact Force Sensor Incorporated in Irrigated Radio frequency Ablation Catheter Predicts Lesion Size and Incidence of Steam Pop and Thrombus", *Circ Arrhythmia Electrophysiol*, 2008 by Yokoyama et al. Too great a contact force may lead to unnecessary damage of healthy tissue, whereas too low a contact force may lead to the creation of incomplete lesions. Moreover, the risk of complications increases dramatically with contact force, in particular with respect to the risk of causing stream pops and thrombus in connection with the ablation. Additionally by applying a too high contact force, the cardiac wall may be affected in a way which leads to electro-anatomic mapping registration errors, cf. "A systematical analysis of in vivo contact forces on virtual catheter tip/tissue surface contact during cardiac mapping and intervention", *J Cardiovasc Electrophysiol*, 2008 by Okumura et al.

The published US patent application 2008/0009750 A1 discloses a catheter for diagnosis or treatment of a vessel or organ. The catheter has in its distal end region incorporated a tri-axial force sensor for detecting the contact force. The force sensor comprises a housing and a plurality of optical fibers in the housing that measure changes in light intensity resulting from deformations of the housing. The deformation is caused by forces applied at the distal extremity of the catheter. The tri-axial force sensor and associated fibers take up space in the distal region of the catheter, moreover a light source is required which adds to the cost of the device.

There is still a need in the art for improved equipment suitable for use in connection with catheter-based surgery.

SUMMARY OF THE INVENTION

It would be advantageous to achieve a force sensor suitable for integration into a medical device, such as a medical probe or catheter, which does not require additional space, or only infers minimal space requirements in the distal end region of the medical device. In general, the invention preferably seeks to mitigate, alleviate or eliminate one or more of the above mentioned disadvantages singly or in any combination. In particular, it may be seen as an object of the present invention to provide a method that solves the above mentioned problems, or other problems, of the prior art.

To better address one or more of these concerns, in a first aspect of the invention a medical ultrasound device is presented that comprises:
- an elongated body having a proximal end, a distal end region and a length axis along the elongation;
- one or more ultrasound transducer for generating acoustic radiation, the one or more ultrasound transducers being positioned in the distal end region, inside the elongated body;
- a transmission element positioned in the radiation path of the acoustic radiation, wherein the transmission element is substantially transparent to acoustic radiation;
- wherein the transmission element and the one or more ultrasound transducers are mounted so that an acoustic path length between the transmission element and the ultrasound transducer varies with contact force imposed to the distal end region.

The invention provides a medical device, such as a catheter or probe, with integrated ultrasound facilities, where the ultrasound radiation can be used for general purposes, as well as for generating a measure of the contact force imposed to the distal end region. In an advantageous embodiment, the one or more ultrasound transducers are capable of generating acoustic radiation suitable for monitoring a region of interest simultaneously with, concurrently with or together with detecting the acoustic path length between the ultrasound transducer and the transmission element. The contact force imposed to the distal end is deduced from the path length. By basing the detection of the contact force on ultrasound radiation and path length detection between the ultrasound transducer and the transmission element, key elements to perform the contact force detection are elements which also may be used for other purposes, and a separate sensor is not needed. The ultrasound transducer(s) may be used for monitoring purposes and a transmission element is always needed in order to couple the acoustic radiation out of the medical device. A compact and cost-effective medical device is therefore provided.

In the context of the present invention, monitoring is to be construed broadly. It includes both 1D monitoring, i.e. detecting reflected intensities along the line of sight as well as 2D imaging where an array of transducers are applied to generate a 2D image. In principle also 3D imaging and time resolved imaging may be obtained. In catheter-based monitoring, it is normal to use 1D or 2D monitoring due to space constraints in the distal end region, i.e. in the tip region.

In general, the transmission element should be substantially transparent to acoustic radiation. A number of materials, including various polymer materials, fulfill this. In general any material can be used, as long as the transparency is sufficient to enable clinical use as well as to enable detection of the acoustic path length through the element. In particular, a material with a transparency to acoustic radiation above 50% may be used, such as above 60%, 70%, 80%, 90%, or even above 95%.

In an advantageous embodiment, the acoustic path length between the ultrasound transducer and the transmission element is detected based on detecting reflected acoustic radiation from a surface of the backside of the transmission element or a surface of the front-side of the transmission element. In particular, the detection of the acoustic path length may be based on a detection of the time of flight, and changes in time of flight, of radiation emitted from the transducer, reflected from a surface of the transmission element, and detected again by the transducer.

In an advantageous embodiment, the medical device further comprises a compressive element positioned in the distal end region, the compressive element being capable of varying its size as a function of an exerted compression force resulting in acoustic path length variations. It is an advantage to use a compressive element since a compressive element can be incorporated into the distal end region in a compact way. Depending on the specific embodiment, a compressive element can be incorporated into the distal end region in a way which does not require additional space in the distal end region, or which only imposes minimal space requirements.

In advantageous embodiments the compressive element, such as a compressive collar, is integrated into the elongated body. In other advantageous embodiments one or more compressive elements, such as one or more spring elements, are integrated into the transmission element or attached to the transmission element.

In an advantageous embodiment the device comprises at least two ultrasound transducers for emitting acoustic radiation along at least two axes. By using two or more ultrasound transducers the force may be detected in two or more (three) dimensions.

Advantageously, the transmission element may comprise a treatment modality for treatment of body tissue. In an embodiment, the treatment modality is ablation, such as radiofrequency (RF) ablation.

In an embodiment the ablation is performed by use of an electrode supported by the transmission element. The electrode may be provided such that the acoustic radiation is substantially unaffected by the presence of the electrode. In an embodiment, the electrode is in the form of a thin layer sufficiently thin to be substantially transparent to acoustic radiation. Acoustic radiation will be transmitted substantially unaffected by the presence of a metal layer with a thickness below 500 nanometers, such as below 250 nanometers, such as with a thickness of 150 nanometers. In other embodiments, the electrode may be in the form of a mesh or other open structures. An electrode in the form of a mesh, with a central aperture or even in the form of a band or ring, may allow radiation to pass, and still be able to work as an RF-electrode. It is an advantage to use a setup which allows for simultaneous force detection and operation of the treatment modality. While force detection may be performed without operation of a treatment modality, it is nevertheless during treatment, such as during ablation, that it is most important to ensure proper contact force between the device and the tissue.

In a second aspect of the invention a medical system is presented. The system comprises a medical device in accordance with the first aspect of the invention and a controller unit operatively connected to the ultrasound transducer, where the controller unit detects the acoustic path length between the ultrasound transducer and the transmission element and determines the contact force from the detected acoustic path length.

In an embodiment where the transmission element further comprises a treatment modality for treatment of body tissue, the treatment modality may be operatively connected to the controller unit, so that the treatment modality is controllable to operate within a pre-specified contact force range. The relevant contact forces may be so small that the medical practitioner is unable to perceive changes in imposed contact force, controlling the treatment modality to operate within a pre-specified contact force range may ensure that the ablative power delivered to the tissue may safely by applied.

In a third aspect of the invention, a method of operating a medical device is presented. A medical device in accordance with the first aspect of the invention is operated by steps which comprise:
  generate acoustic radiation by operating the one or more transducers in a generation mode;
  detect reflected acoustic radiation by operating the one or more transducers in a detection mode;
  from the reflected acoustic radiation detect the acoustic path length between the transmission element and the ultrasound transducer;
  determine the contact force from the detected acoustic path length.

In a fourth aspect of the invention, a computer program product is presented that is adapted to enable a computer system comprising at least one computer having data storage means associated therewith to operate a medical device according to according to the first or second aspects of the invention or to carry out the steps of the third aspect of the invention.

In general the various aspects of the invention may be combined and coupled in any way possible within the scope of the invention. These and other aspects, features and/or advantages of the invention will be apparent from and elucidated with reference to the embodiments described hereinafter.

BRIEF DESCRIPTION OF THE DRAWINGS

Embodiments of the invention will be described, by way of example only, with reference to the drawings, in which
  FIG. 1 schematically illustrates the distal end region of an ablation catheter-based probe.

DESCRIPTION OF EMBODIMENTS

The present invention is disclosed in connection with a RF ablation catheter comprising a monitoring system in accordance with embodiments of the present invention. It is however to be understood that, while such an application is advantageous, the invention is not limited to this. In fact, the medical device may be applied in connection with any device which uses ultrasound transducers and which supports a structural configuration which enables that an acoustic path length between a transmission element and the ultrasound transducer varies with contact force imposed to the distal end region.

Figure 1:
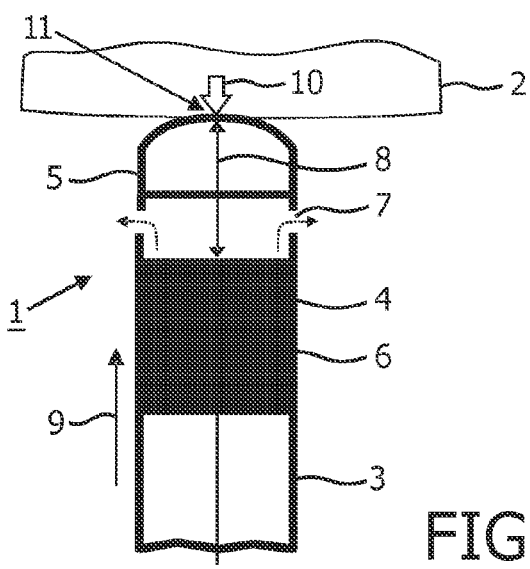

FIG. 1 schematically illustrates the distal end region 1 of an ablation catheter-based probe, hereafter simply referred to as a catheter, abutting an object 2, such as tissue in the form of a cardiac wall. The catheter comprises an elongated body 3, a distal end region 1 and a proximal end (not shown). A length axis 9 runs along the elongation of the elongated body. The distal end region 1 is the extended end section of the elongated body 3 abutting the distal end itself 11. The catheter may at the proximal end be connected to a controller unit (cf. FIG. 11) so as to form a medical system. The ultrasound transducer 4 is housed in the distal end region, where it is fixed by suitable means 6. The catheter comprises a transmission element 5 positioned in the radiation path of the acoustic radiation. The transmission element may be used as a transmission window for coupling the acoustic radiation out of the medical device. The transmission element has a backside generally facing the ultrasound transducer and an opposite facing front-side. The transmission element is substantially transparent to acoustic radiation, so that radiation generated by the ultrasound transducer will be transmitted through the transmission element to interact with the tissue 2 under investigation or treatment. In an embodiment, the acoustic radiation is emitted along the length axis 9.

As is illustrated in FIG. 1, the distal end region may further comprise fluid channels 7 which allow delivery of fluid through the elongated body to the distal end region so as to irrigate the treatment site during treatment if this is necessary or desirable, typically by use of saline fluid pumped from a reservoir placed at the proximal end. The fluid channels may be holes into the side of the tube as in the illustrated embodiment, or made by other suitable means.

In an embodiment the device may e.g. be an ultrasound catheter with an integrated ablation electrode. The ultrasound catheter supports monitoring of tissue properties by operating the ultrasound transducer in a monitoring mode, where ultrasound pulses are emitted and the reflected radiation is detected in order to generate an ultrasound image or scan. Operating an ultrasound transducer for detecting reflected radiation is known to the skilled person.

The elongated body may be of a flexible material, such as a suitable polymer material for use in connection with a medical device. Such materials are known to the skilled person. A flexible device is thereby obtained. Alternatively may the elongated body be made of a rigid material, such as surgical steel or other suitable materials as are known to the skilled person. A rigid device may e.g. be implemented as a needle device.

The transmission element and the ultrasound transducer are mounted so that an acoustic path length between the transmission element and the ultrasound transducer varies with contact force imposed to the distal end region. That is, if the catheter tip is pressed into the tissue 2, the acoustic path length changes with exerted force 10. The acoustic path length may e.g. be expressed as the length 8 between the top face of the ultrasound transducer and the front-surface of the transmission element. The detection of the acoustic path length is controlled by the controller unit, which from the detected path length determines the contact force.

Figure 2:
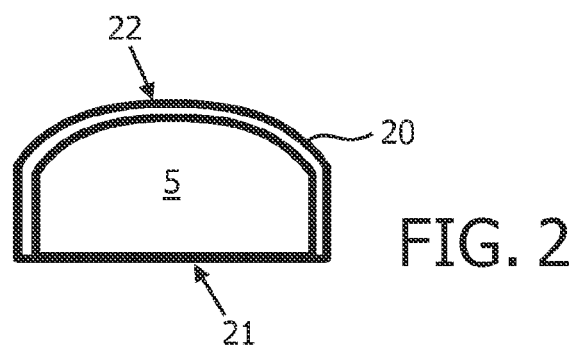
FIG. 2 schematically illustrates an ablation electrode supported by a transmission element.

FIG. 2 schematically illustrates an ablation electrode 20 supported by a transmission element 5. The transmission element has a backside 21 and a front side 22. The ablation electrode may be formed by a thin conducting layer supported by the transmission element. In an embodiment, the transmission element comprises a polymer-based body and a conducting layer. The polymer-based body may be of the material poly-methylpentene (TPX) which is commonly used in connection with ultrasound, whereas the conducting layer may be a metallic layer, such as a platinum layer. Suitable thicknesses may be a few hundred micrometers thick TPX supporting a few hundred nanometer thick platinum layer, such as a 250 micrometer thick TPX element, supporting a 150 nanometer thick platinum layer. The thickness of the TPX element is the thickness at the central region. Other materials may also be used, as long as they are sufficiently transparent to acoustic radiation. The transmission element and supported electrode are illustrated in a rounded configuration which is the clinically relevant shape. In general any shape may be used.

Figure 3:
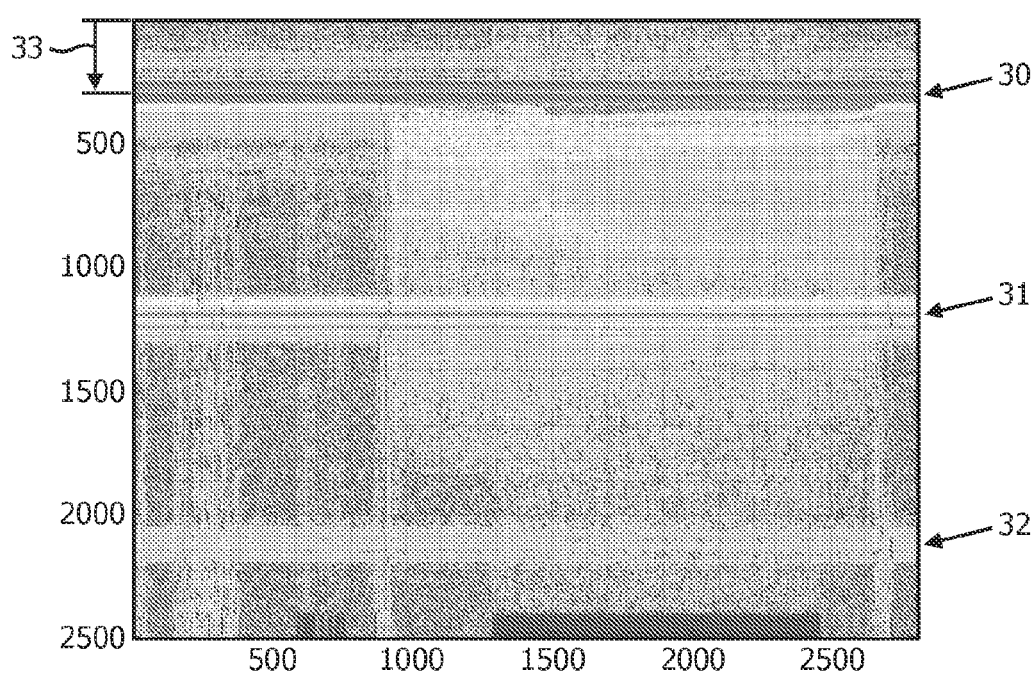
FIG. 3 illustrates a screen shot of an M-mode ultrasound image of cardiac ablation in a sheep heart.

FIG. 3 illustrates a screen shot of an M-mode ultrasound image of cardiac ablation in a sheep heart as generated by an ablation catheter of the type schematically illustrated in FIG. 1. The vertical axis show the distance from the transducer. The distance is given in pixels which can be converted into time or depth. The horizontal axis illustrates time, again given in pixels (increments of 20 pixels equals 1 second). The image shows the strong primary reflection 30 from the TPX/Pt ablation electrode, and in addition 2nd and 3rd order reflection peaks 31, 32. The positions of these reflections are related to the time-of-flight of the ultrasound signal, and therefore the distance from the ultrasound transducer to the ablation electrode. The distance between the ultrasound transducer and the TPX element, can therefore be determined with an accuracy equal to the axial resolution of the ultrasound. At an imaging frequency of 20 MHz, this resolution is equal to the axial resolution of the ultrasound. At an imaging frequency of 20 MHz, this resolution is equal to 0.04 mm (half the wavelength) or 5 pixels (given a sampling frequency of 200 MHz).

A distance change between the ultrasound transducer and the ablation electrode (ref numeral 8 on FIG. 1), results in a change in position (ref numeral 33 on FIG. 3) of the ablation electrode's reflection on the M-mode image changes. The distance change, hereafter referred to as ΔL, can be measured by the controller unit, which based on the measured ΔL, can determine the contact force.

Figure 4:
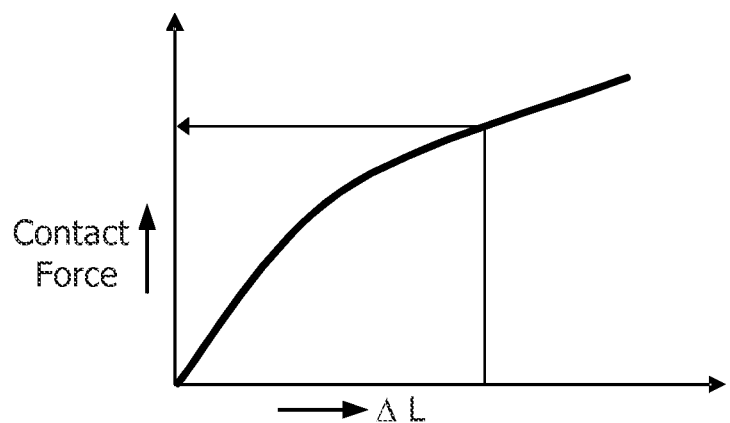
FIG. 4 schematically illustrates a functional relationship between ΔL along the horizontal axis and the contact force along the vertical axis.

FIG. 4 schematically illustrates a functional relationship between ΔL along the horizontal axis and the contact force along the vertical axis. The determination of the contact force can be done in terms of a functional relationship, a look-up table or by any other suitable means. The relationship between ΔL and contact force, can either be determined beforehand by the provider of the medical device, or it may be calibrated by the user and the calibration result stored in the controller unit. Having realized that the contact force can be determined from positioning of the reflection peaks, a practical implementation of a suitable algorithm is within the capabilities of the skilled person. Use of look-up tables or functional relationships facilitates fast and flexible ways of correlating the measured path length to the contact force during clinical use.

In order to vary ΔL with contact force, the distal end region may comprise a compressive element, where the compressive element is capable of varying its size as a function of an exerted compression force. Since the size of the compressive element varies, also the acoustic path length varies. FIGS. 5-8 illustrate embodiments of catheters provided with different types of compressive elements in the distal end region.

Figure 5:
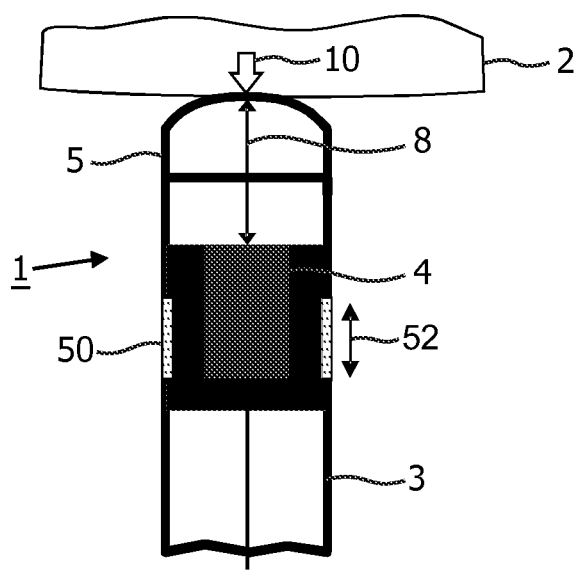
FIG. 5 illustrates an embodiment of a medical device with a compressive element in the form of a compressive collar integrated into the elongated body.

FIG. 5 illustrates an embodiment of a medical device with a compressive element 50. The compressive element is in the form of a compressive collar 50 integrated into the elongated body, typically in the distal end region, as a circumferential band mounted in the elongated body. A contact force 10 exerted on the catheter tip will reduce the length 52 of the compressive collar by an amount ΔL. As a result, the distance 8 from the ultrasound transducer to the front-surface of the transmission element will be reduced by the same amount. The compressive element may be mounted at any appropriate position along the length axis of the elongated body.

The magnitude of ΔL depends on the Young's modulus, Y, of the material from which the compressible collar is formed:

$$F = \frac{Y \cdot \Delta L \cdot A}{L}$$

where F is the contact force, L is the length of the non-compressed collar and A the cross-sectional area of the compressive collar. This equation holds if R/t<10, where R is the radius of the collar and t is the thickness of the collar. This equation would e.g. apply for a 2.5 mm diameter catheter with a collar thickness of t=0.2 mm. If R/t>10, the following equation applies:

$$F = \frac{Y \cdot \Delta L \cdot t}{L}$$

For a 20 MHz ultrasonic image the resolution is 0.04 mm, therefore distance changes greater than this can be measured accurately. In a 7.5 F imaging catheter, a compressible collar with a length of 3 mm that is made from a material with a Young's modulus of 0.15 MPa will compress by a ΔL of 0.05 mm for every 5 grams (~0.05N) of contact pressure. Silicone elastomeres, some forms of rubber, and very low-density polyethylene (LDPE) have Young's moduli in this range and are biocompatible. Silicone elastomeres have the advantage that they are heat resistant from −70 to 250° C., whereas rubber and LDPE may only be resistant to 100° C. This temperature is however still high enough for most, if not all, ablation applications. The thickness of the collar and its elasticity are important. A ΔL of only 0.05 mm for every 5 g change in contact pressure will have negligible effect on the catheter tip's handling (i.e. on it's perceived softness, flexibility etc). In embodiments, contact pressures rounded to the nearest 5 g can thus be determined. This information would allow the physician to maintain a contact force within the optimal range of 10-20 g. If the compressible collar requires structural support, it could be reinforced with a spring-like braid along its inner surface (whose spring constant matches that of the collar material). In embodiments, the material of the compressive element has a Young's modulus in the range of 0.05 MPa to 0.30 MPa, such as in the range 0.1 MPa to 0.25 MPa, such as in the range 0.15 MPa to 0.2 MPa. In embodiments, the collar thickness may be in the range of 0.05 mm to 0.5 mm, such in the range of 0.1 mm to 0.4 mm, such in the range of 0.2 mm to 0.3 mm. In embodiments, the material of the compressive element may be selected so that the compressive element is compressible by a compression force in the range of 0.05N to 0.5N, such as in the range of 0.1N to 0.4N, such as in the range of 0.2N to 0.3N.

Figure 6A:
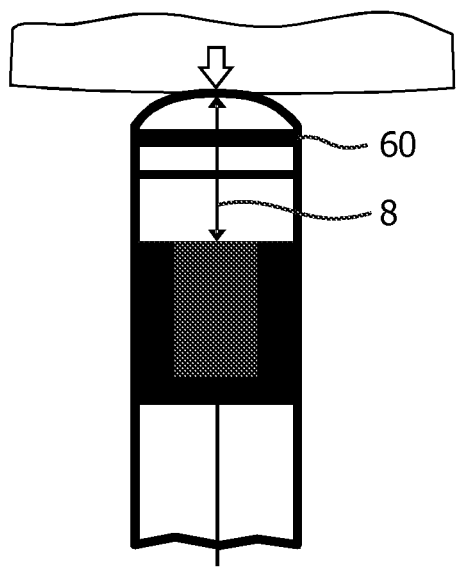
FIGS. 6A and 6B illustrate an embodiment of a medical device with a compressive element integrated into (A) and attached to (B) the transmission element.

FIG. 6A illustrates an embodiment of a medical device where the compressive element is a spring element 60 integrated into the transmission element. The spring element may be a mechanical spring. A change of ΔL of the spring reduces the distance 8 from the ultrasound transducer to the front-surface of the transmission element with the same amount, given that the rest of the catheter tip is non-compressible. The mechanical spring can be such elements as a coil, a hollow cylindrical mesh or a slab of resilient material. The spring may have a spring constant, k, of approximately 1000 N/m (thus a 5 g force would lead to a tip compression of 0.05 mm), such as a spring constant in the range of 750 N/m to 1250 N/m. In an embodiment, the spring is made from an electrically conductive material so that electrical current flows through it into the tip of the electrode. In a further embodiment, the pitch of the spring can be used as fluid channels for irrigation. In the illustrated embodiment, the spring element is positioned centrally with respect to the transmission element. In other embodiments, the positioning of the spring element may be displaced towards one end of the transmission element.

Figure 6B:
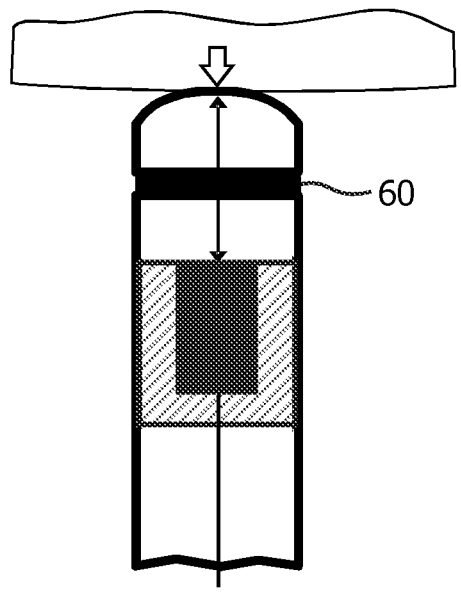

FIG. 6B illustrates an embodiment of the medical device with a spring element in the form as disclosed above in connection with FIG. 6A. However, instead of integrating the spring element into the transmission element, the spring element is attached to the backside of the transmission element, so that the spring element interconnects the elongated body and the transmission element.

Figure 7:
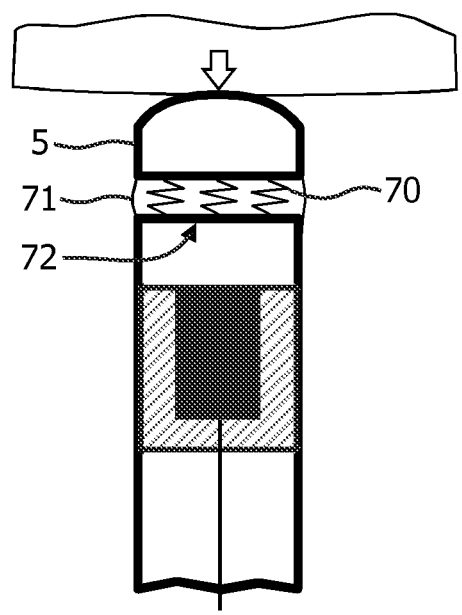
FIG. 7 illustrates an embodiment of a medical device where the transmission element is attached in the distal end region of the elongated body by means of one or more compressive elements.

FIG. 7 illustrates an embodiment of a medical device where the transmission element 5 is attached in the distal end region 72 of the elongated body by means of one or more compressive elements 70, and wherein the region between the elongated body and the transmission element is covered by a compliant material 71 enveloping the region. In the illustrated embodiment three spring elements are positioned in the cross-sectional area between the elongated body and the transmission element. The spring elements are protected by a balloon-like thin foil 71. In an embodiment, the foil is made from a sufficiently thin material, so that it does not contribute to the total spring constant. Moreover, the foil may be made longer than the springs in their extreme position, which is schematically illustrated by the bulging of the foil. The total spring constant, k, should again be of approximately 1000 N/m (thus a 5 g force would lead to a tip compression of 0.05 mm), such as a total spring constant in the range of 750 N/m to 1250 N/m.

In a clinical setting, the catheter tip may be held both perpendicular and parallel to the heart tissue, and therefore, contact forces may be both perpendicular and parallel to the length axis of the catheter.

Figure 8:
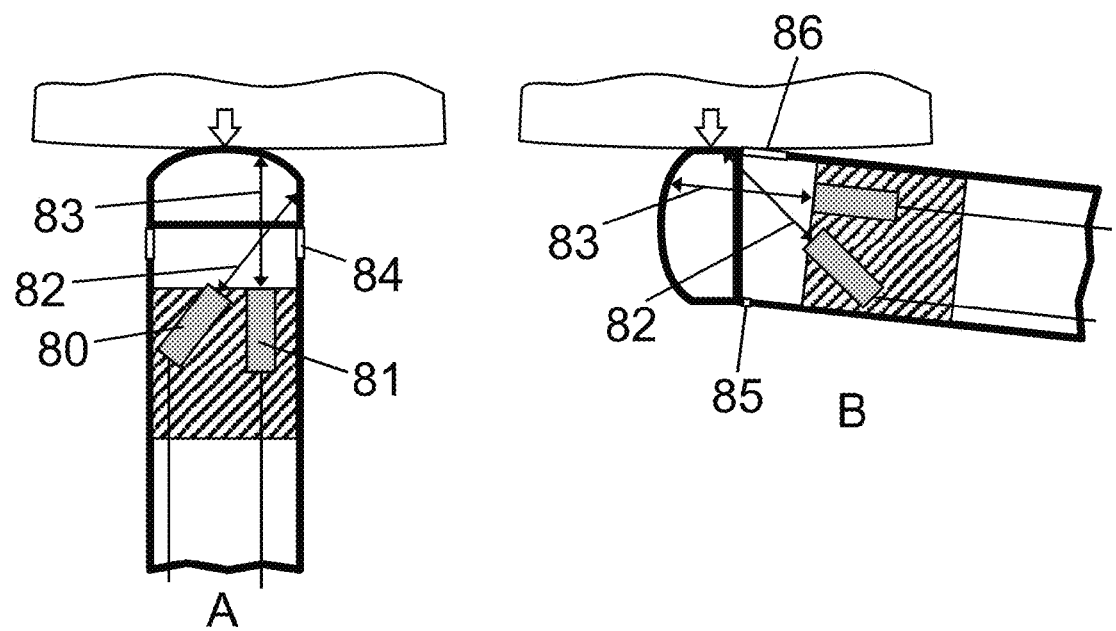
FIGS. 8A and B illustrate an embodiment of a medical device with two ultrasound transducers.

FIG. 8 illustrates an embodiment of a medical device where the device comprises at least two ultrasound transducers 80, 81, a first ultrasound transducer for emitting acoustic radiation along the length axis 82, and at least a second ultrasound transducer for emitting acoustic radiation along an axis 83 which is tilted with respect to the length axis. The acoustic path length between the transmission element and the first ultrasound transducer is detected and the acoustic path length between the transmission element and the at least second ultrasound transducer is detected, and the acoustic path length changes along the length axis and at least along the axis which is tilted with respect to the length axis are thereby detected. In the illustrated embodiment, two transducers are shown however three or more may be used. In particular, three transducers can advantageously used in order to detect the acoustic path length changes along three spatial axes to determine the 3D displacement of the catheter tip. In an embodiment, the catheter may monitor at multiple viewing angles using fluid lens or multiple single-element transducers. The contact force can be determined similarly as with a single transducer. It can be calculated directly if the relationship between all ΔL's and the contact force is well-defined. Otherwise, a look-up table may be used.

In the illustrated embodiment, the medical device further comprises a compressive collar 84 positioned between the transmission element and the elongated body. The contact pressure changes the distance 82, 83 between the ablation electrode and each ultrasound transducer; in the case of the fluid-lens, it changes the profile of the ablation electrode on the B-mode image. As illustrated in FIG. 8B, if the contact pressure is perpendicular to the catheter axis, the compressible collar deforms slightly 85, 86 and the catheter tip is pushed slightly to the side (the bend angle is highly exaggerated in the Figure for illustration purposes). It is expected that the collar deformation would be at most 0.5 mm off-axis (at the maximum expected contact pressure of ~50 g), which is neither significant enough to affect catheter tip contact with the tissue nor to change the catheter handling properties.

In an embodiment, the treatment modality is operatively connected to the controller unit, so that the treatment modality is controllable to operate within a pre-specified contact force range.

Figure 9:
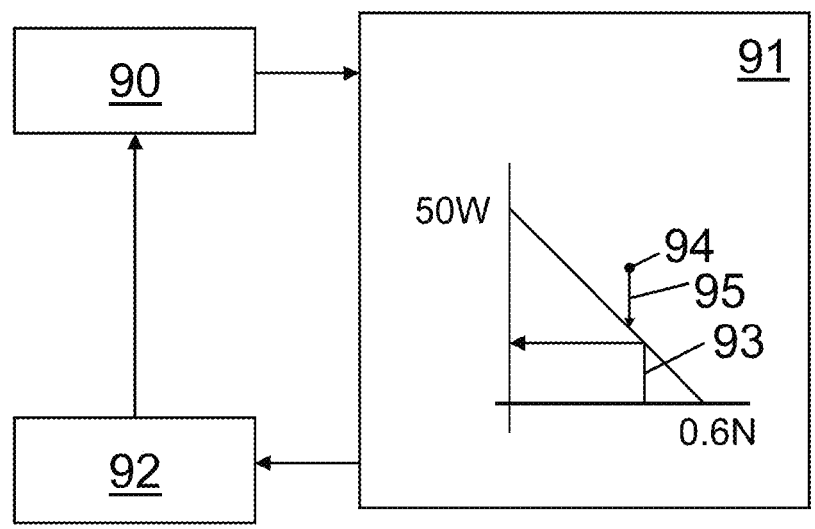
FIG. 9 schematically illustrates a flow chart of a feedback loop which may be used to automatically regulate the ablative power applied through the catheter tip based on the contact force between the catheter tip and tissue.

FIG. 9 schematically illustrates a flow chart of a feedback loop which may be used to automatically regulate the ablative power applied through the catheter tip based on the contact force between the catheter tip and tissue. Yokoyama et al. as referred to in the section background of the invention, have found that the ablative power that can be safely applied to tissue is heavily dependent on the contact force; in their study, at moderate RF power (30 W), steam pops occurred only with 0.4N or more of contact force while at 50 W, steam pops occurred at contact forces as low as 0.1N (and furthermore the incidence of a steam pop increased significantly with increasing force). Based on this a feedback loop in which the power applied is inversely related to the power setting may be used. FIG. 9 schematically illustrates an implementation 91 of the relationship between optimal power setting (vertical axis) and contact force (horizontal axis). It is illustrated to be linear-inverse, in general the specific relationship should be optimized through animal studies, and will not necessarily be linear-inverse. In a situation of use, the relationship 91 between optimal power setting and contact force may be determined based on a computation performed by the controller unit or a computing unit in or connected to the controller unit.

In FIG. 9, the contact force is measured 90, and based on this measurement the optimal power setting is determined 93. In an embodiment, the operational power of the ablation electrode is set 92 to the optimal power at the measured contact force, and the contact force is measured anew.

In another embodiment, the feedback loop is used to control that the maximum power does not exceed the optimal power. Thus, if the actual power used 94 is higher than the optimal power at the specific contact force, the operation power is down-scaled 95 to the optimal power, while the contact force is too high.

Figure 10:
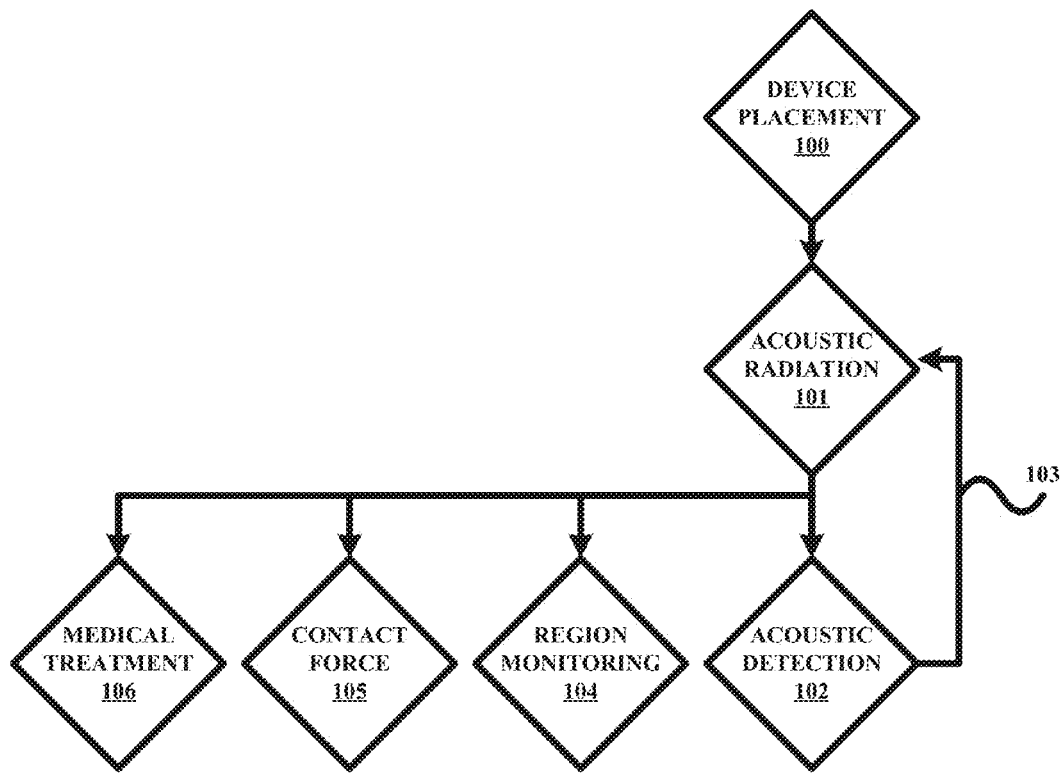
FIG. 10 illustrates a flow diagram of steps which may be performed in order to operate a medical device in accordance with embodiments of the present invention.

FIG. 10 illustrates a flow diagram of some of the steps which may be performed in order to operate a medical device in accordance with embodiments of the present invention. Firstly, the medical device may be positioned 100 in the region of interest, for example in close proximity of cardiac tissue to undergo ablation treatment. The transducers are operated to generate 101 acoustic radiation and to detect 102 the reflected acoustic radiation. The transducers may be operated continuously 103 during the investigation and treatment. The reflected acoustic radiation is detected in order to monitor 104 the region of interest during the procedure, and from the reflected acoustic radiation also the acoustic path length is deduced to determine the contact force 105. Simultaneously with the monitoring and the contact force detection, the treatment modality may be operated 106 in order to perform medical treatment. For example, the tissue under treatment may undergo ablation.

Different types of compressive elements have been disclosed. It is to be understood that even though some features have been disclosed in connection with specific embodiments, features disclosed for one embodiment may within the scope of the claims be combined with features disclosed for a different embodiment.

Figure 11:
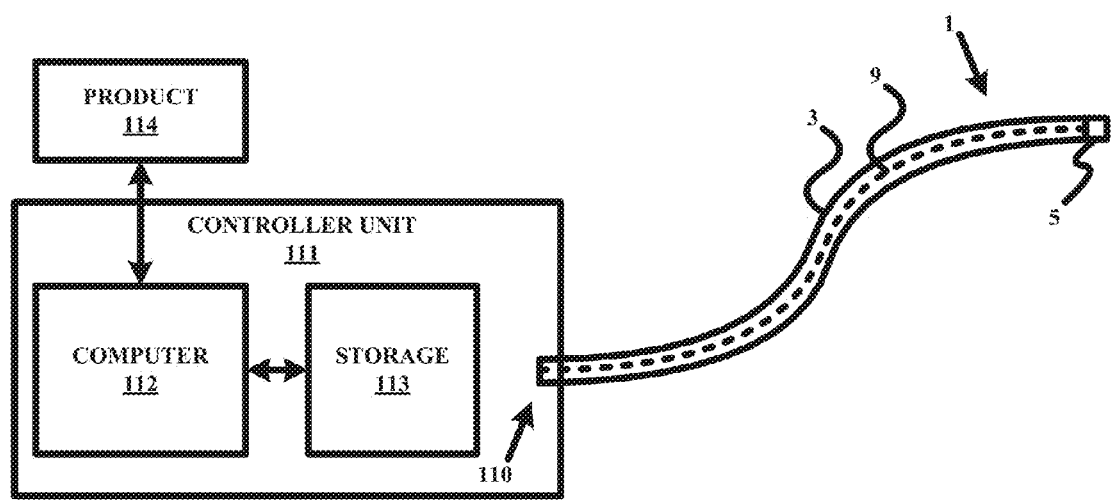
FIG. 11 schematically illustrates a medical system in connection with a computer program product.

FIG. 11 schematically illustrates a medical system in connection with a computer program product. The medical system comprises a catheter in accordance with embodiments of the present invention. The catheter comprises an elongated body 3 having a proximal end 110, a distal end region 1 and a length axis 9 along the elongation. Moreover, the catheter comprises one or more ultrasound transducers positioned in the distal end region and a transmission element 5 positioned at the extremity of the elongated body to couple acoustic radiation in and out of the catheter.

The catheter may at the proximal end 110 be connected to a controller unit 111, such as a dedicated purpose or general purpose computing unit for control of at least the ultrasound transducer(s) and for dealing with the signal treatment and extraction of detection results. To this end, the detection of the acoustic path length between the ultrasound transducer and the transmission element and the determination of the contact force from the detected acoustic path length is controlled by the controller unit 111.

The controller unit may implement a computer system 112, such as a dedicated purpose or general purpose computing unit for controlling the system. The computer system may comprise storage means 113 for storing data which may be needed to operate the medical system or to store any acquired data, or for any other purpose where storage of data is desired. The computing system may be adapted to receive instructions from a computer program product 114 in order to operate the system. The computer program product may be comprised in a data carrier as illustrated in the Figure, however once loaded into the computer system it may be stored by, and run from, the storage means 113.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A medical ultrasound device comprising:
an elongated body having a proximal end, a distal end region and a length axis along the elongation;
one or more ultrasound transducers for generating acoustic radiation, the one or more ultrasound transducers being positioned in the distal end region, inside the elongated body; and
a transmission element positioned in the radiation path of the acoustic radiation,
wherein the transmission element is substantially transparent to acoustic radiation and
wherein the transmission element and the one or more ultrasound transducers are mounted so that an acoustic path length between the transmission element and each ultrasound transducer varies with contact force imposed to the distal end region.

2. The device according to claim 1,
wherein the transmission element has a backside generally facing the ultrasound transducer and an opposite facing front-side, and
wherein the acoustic path length is detected based on detecting reflected acoustic radiation from a surface of the backside of the transmission element or a surface of the front-side of the transmission element.

3. The device according to claim 1, further comprising:
a compressive element positioned in the distal end region,
wherein the compressive element is capable of varying its size as a function of an exerted compression force, and
wherein the acoustic path length varies as a function o he size of the compressive element.

4. The device according to claim 3, wherein the compressive element is compressible by a compression force in the range of 0.05N to 0.5N.

5. The device according to claim 3, wherein the compressive element is integrated into the elongated body.

6. The device according to claim 3, wherein the compressive element is in the form of one or more compressive elements integrated into the transmission element or attached to the transmission element.

7. The device according to claim 1,
wherein the transmission element is attached in the distal end region of the elongated body by one or more compressive elements, and
wherein the region between the elongated body and the transmission element is covered by a compliant material enveloping the region.

8. The device according to claim 1, wherein the one or more ultrasound transducers include at least two ultrasound transducers, a first ultrasound transducer for emitting acoustic radiation along a length axis, and at least a second ultrasound transducer for emitting acoustic radiation along an axis which is tilted with respect to the length axis, so that the acoustic path length between the transmission element and the first ultrasound transducer is detected and the acoustic path length between the transmission element and the at least second ultrasound transducer is detected, thereby detecting the acoustic path length changes along the length axis and at least along the axis which is tilted with respect to the length axis.

9. The device according to claim 1, wherein the transmission element includes a polymer-based body which is substantially transparent to acoustic radiation, covered with an electrode substantially transparent to acoustic radiation.

10. The device according to claim 1, wherein the transmission element includes a treatment modality for treatment of body tissue.

11. The device according to claim 1, wherein the device is an ultrasound catheter with an integrated ablation electrode, wherein the transmission element includes the integrated ablation electrode.

12. A medical system comprising:
an elongated body having a proximal end, a distal end region and a length axis along the elongation;
one or more ultrasound transducers for generating acoustic radiation, the one or more ultrasound transducers being positioned in the distal end region, inside the elongated body;
a transmission element positioned in the radiation path of the acoustic radiation, wherein the transmission element is substantially transparent to acoustic radiation;
a controller unit operatively connected to the ultrasound transducer;
wherein the transmission element and the one or more ultrasound transducers are mounted so that an acoustic path length between the transmission element and each ultrasound transducer varies with contact force imposed to the distal end region; and
wherein the controller unit is configured to detect each acoustic path length between each ultrasound transducer and the transmission element and determines the contact force from each detected acoustic path length.

13. The system according to claim 12,
wherein the transmission element includes a treatment modality for treatment of body tissue, and
wherein the treatment modality is operatively connected to the controller unit, so that the treatment modality is controllable to operate within a pre-specified contact force range.

14. Method of operating a medical device, the device includingan elongated body having a proximal end, a distal end region and a length axis along the elongation;
one or more ultrasound transducers for generating acoustic radiation, the one or more ultrasound transducers being positioned in the distal end region, inside the elongated body;
a transmission element positioned in the radiation path of the acoustic radiation, wherein the transmission element is substantially transparent to acoustic radiation;
wherein the transmission element and the one or more ultrasound transducers are mounted so that an acoustic path length between the transmission element and each ultrasound transducer varies with contact force imposed to the distal end region;
wherein the method comprises
generate acoustic radiation by operating the one or more transducers in a generation mode;
detect reflected acoustic radiation by operating the one or more transducers in a detection mode;
from the reflected acoustic radiation, detect an acoustic path length between the transmission element and each ultrasound transducer;

determine the contact force from each detected acoustic path length.

15. A computer program product being adapted to enable a computer system comprising at least one computer having data storage means associated therewith to operate a medical device according to claim 1.

* * * * *